United States Patent [19]

Tsai et al.

[11] Patent Number: 5,366,659

[45] Date of Patent: Nov. 22, 1994

[54] FERROELECTRIC LIQUID CRYSTALS CONTAINING PYRIMIDINE AND CHIRAL COMPOUNDS AND LIQUID CRYSTAL COMPOSITIONS CONTAINING THE SAME

[75] Inventors: Wen-Liang Tsai, Hsing-Ying; Hwei-Long Kuo, Taipei; Shih-Yiing Sheu, Tainan, all of Taiwan, Prov. of China

[73] Assignee: Industrial Technology Research Institute, Hsinchu, Taiwan, Prov. of China

[21] Appl. No.: 215,525

[22] Filed: Mar. 22, 1994

[51] Int. Cl.$^5$ .............. C09K 19/34; C09K 19/52; C07C 41/00; C07D 239/02
[52] U.S. Cl. .............. 252/299.61; 544/298; 568/631; 568/647; 252/299.01
[58] Field of Search ............ 252/299.61, 299.01; 544/298; 568/631, 647

[56] References Cited

U.S. PATENT DOCUMENTS

| | | |
|---|---|---|
| 4,900,472 | 2/1990 | Miyazawa et al. ............ 252/299.61 |
| 4,980,083 | 12/1990 | Shibata et al. ............ 252/299.61 |
| 5,013,475 | 5/1991 | Shibata et al. ............ 252/299.61 |
| 5,043,094 | 8/1991 | Takano et al. ............ 252/299.61 |
| 5,080,827 | 1/1992 | Miyazawa et al. ............ 252/299.66 |
| 5,152,919 | 10/1992 | Kitamura et al. ............ 252/299.61 |
| 5,236,618 | 8/1993 | Heppke et al. ............ 252/299.61 |

*Primary Examiner*—Richard D. Lovering
*Assistant Examiner*—C. Harris
*Attorney, Agent, or Firm*—W. Wayne Liauh

[57] ABSTRACT

A liquid crystal composition containing an optically active or a ferroelectric liquid crystal compound represented by the following formula:

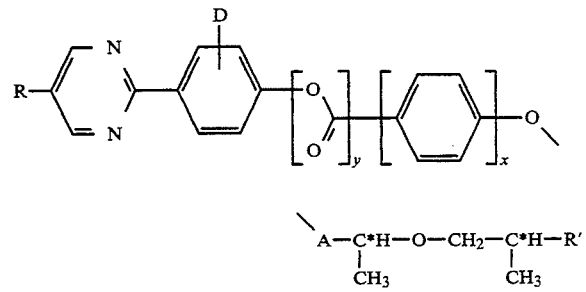

wherein A can be either —$CH_2$— or —CO—; R can be either an alkyl or alkoxyl group having 1 to 22 carbons: R' is an alkyl group having 2 to 8 carbons; x and y are integers of either 0 or 1, provided that when x=0, y≠1; D can be a hydrogen or a halogen atom; and * represents a chiral center. The ferroelectric liquid crystals of the present invention exhibit optical and chemical stabilities, high-speed responsive, and high spontaneous polarization, and thus are excellent materials for use in making liquid crystal devices and liquid crystal light switching elements.

14 Claims, No Drawings

FERROELECTRIC LIQUID CRYSTALS CONTAINING PYRIMIDINE AND CHIRAL COMPOUNDS AND LIQUID CRYSTAL COMPOSITIONS CONTAINING THE SAME

FIELD OF THE INVENTION

This invention relates to a family of ferroelectric liquid crystal compounds containing pyrimidine, and chiral compounds and liquid crystal compositions containing; at least one of the ferroelectric liquid crystal compounds. More particularly, this invention relates to a family of novel ferroelectric liquid crystal compounds, and chiral compounds and liquid crystal compositions containing the same, which can be used in making liquid crystal display materials.

BACKGROUND OF THE INVENTION

Liquid crystal compounds are an important part of the liquid crystal display devices. Liquid crystal displays have many outstanding advantages in, for example, that they can be made to exhibit thin-thickness and light-weight, require low driving voltage and low power consumption. Also, they are non-emissive and are easy on the eyes. Because of these advantages, liquid crystal displays are widely considered as the mainstream display devices of the next generation.

Most of the conventional liquid crystal display compounds are of the nematic phase, with the TN-mode (twisted nematic mode) being the most commonly used driving method. However, in their use as a flat panel display, the TN display system has several limitations due to their relatively slow response time and narrow viewing angle, compared to the emissive type display systems such as electrolumilescence displays and plasma displays. Therefore, in order to broaden the acceptance of liquid crystal display devices and utilize the advantages thereof as illustrated hereinabove, developments of improved liquid crystal materials as alternative to the nematic phase type liquid crystal and improved driving methods are essential.

Recently, ferroelectric liquid crystals have received significant attention as an alternative to the nematic type liquid crystals. In the past decade and half, over 500 patents have been issued in the areas related to ferroelectric liquid crystals. The existence of ferroelectric liquid crystals was first observed in 1974 which was subsequently published in 1975 by R. B. Meyer, L. Liebert, L. Strzelecki, and P. Keller (see J. Physique Letters, 1975, 36, L-69). They reported that strong ferroelectricity could be observed from liquid crystals belonging to a chiral smectic C phase (Sc* phase). Prior to the discovery by Meyer, ferroelectricity was observed only in salt crystals. Meyer and his coworkers believed that ferroelectricity may be observed in optically active compounds with a tilted nematic liquid crystal phase. They synthesized a liquid crystal compound (S)-4-n-decyloxybenzylideneamino-2'-methylbutyl cinnamate (DOBAMBC) to prove their theory. Therefore, in theory, any optically active compound that exhibits tilted smectic phase can possess ferroelectricity. Currently, the chiral smectic C-phase (Sc*) compounds are receiving the most attention.

In 1980, N. A. Clark and S. T. Lagerwall proposed a liquid crystal display system wherein an optical switching phenomenon of a ferroelectric liquid crystal was utilized. (See Appl. Phys. Lett., 1980, 36, 899; see, also, U.S. Pat. No. 4,367,924, entitled "Chiral Smectic C or H Liquid Crystal Electro-Optical Device"). The discovery of Clark and Lagerwall opened the door for ferroelectric liquid crystals to be used in practical applications. One of the improvements advanced from their discovery is the use of surface stabilized ferroelectric liquid crystal device (SSFLCD) as a driving mechanism.

In order for the ferroelectric liquid crystals to be used as a display material, many conditions must be met. For example, the temperature range in which the Sc* phase is observed must be wide, and it must include room temperature. Furthermore, it must have high spontaneous polarization, Ps, in order to reduce the response time $\tau$. The relationship between the spontaneous polarization Ps and the response time $\tau$ is shown below:

$$\tau = \eta / Ps \times E \tag{1}$$

wherein $\eta$ is the viscosity of the ferroelectric liquid crystal, and E is the externally applied electrical voltage. From Eqn. (1), it is apparent that the response time of a ferroelectric liquid crystal can be reduced through appropriate molecular design to emphasize certain desired molecular characteristics. For example, a proper increase in the polarity of the ferroelectric molecule can increase the spontaneous polarization thereof and thus reduce the response time. However, Eqn. (1) also shows that viscosity is another important factor affecting the response time. Thus, in designing a ferroelectric molecule, we need to pay attention not only to the spontaneous polarization, but also to the viscosity of the molecule.

In practical applications, since a single molecule may not exhibit all the desired characteristics, a mixture of ferroelectric liquid crystals of various types, rather than a single type, are often used. The mixture can be prepared using doping or mixing methods (See W. Kuczynski, H. Stegemeyer, Chem. Phys. Lett., 1980, 70, 123; S. M. Kelly, A. Villiger, Displays, 1990, 41.) Under these circumstances, the compatibility between or among the various molecules becomes an important consideration.

SUMMARY OF THE PRESENT INVENTION

The primary object of the present invention is to develop a family of novel ferroelectric liquid crystal compounds containing pyrimidine, and chiral compounds liquid crystal compositions comprising the same, which exhibit excellent optical and chemical stabilities, high degree of spontaneous polarization, low viscosity, and fast response time and thus can be used as an excellent base material in the manufacturing of liquid display devices. In the present invention, a liquid crystal compound refers to a liquid crystal molecule, and a liquid crystal composition refers to a liquid crystal mixture containing at least one liquid crystal molecule.

The family of ferroelectric liquid crystal compounds disclosed in the present invention are pyrimidine-containing liquid crystals having two chiral centers represented generally by the following formula:

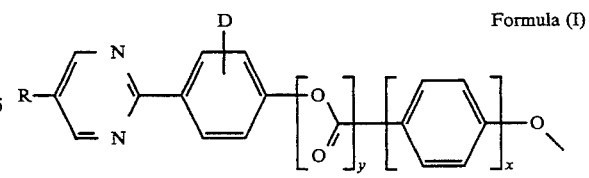

Formula (I)

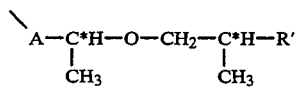

wherein:
A: is selected from the group consisting of —CH$_2$— and —CO—

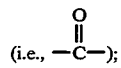

R: is an alkyl or alkoxyl group having 1 to 22 carbons;
R': is an alkyl group having 2 to 8 carbons;
x,y: are integers of either 0 or 1, provided that when x=0, y≠1;
D: is selected form the group consisting of hydrogen and halogen atoms; and
*: represents a chiral center.

Preferably, R is an alkyl group having 3 to 12 carbon atoms; R' is an ethyl group; and D is a hydrogen or fluorine atom.

The liquid crystal composition disclosed in the present invention can comprise one or more of the ferroelectric liquid crystal compounds represented by formula (I). Optionally, the liquid crystal composition disclosed in the present invention can be a mixture which comprises one or more of the ferroelectric compounds represented by formula (I), and a smectic C phase (Sc phase) liquid crystal, or a chiral Sc* phase liquid crystal. The present invention also discloses a liquid crystal device containing one or more of the compounds represented by formula (I), or a mixture containing the same, confined between two electrode substrates. The compound represented by formula (I), or a mixture containing the same, can also be used in making light switching element. The dual chiral centers shown in formula (I) enable the compounds of the present invention to exhibit improved characteristics as ferroelectric liquid crystals.

DETAILED DESCRIPTION OF PREFERRED EMBODIMENT

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

Preparation of Precursory Compound

A precursory compound, which was presented by the following formula as Compound 1:

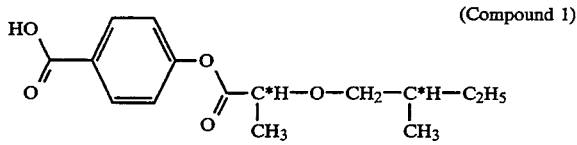

(Compound 1)

was first prepared according to the following steps:

Step A 4.3 g (20 mmol) of 4-hydroxybenzoic acid (from Aldrich, U.S.A.) was dissolved into 20 ml of dimethyl formamide (DMF) to form "solution A". Then 3.5 g (20 mmol) of benzyl bromide (also from Aldrich, U.S.A.) was dissolved into 10 ml of DMF to form "solution B". Solution A was gradually injected, using a syringe, into a 100-ml round-bottomed flask containing 1.6 g (40 mmol) of 60% NaH and 10 ml of DMF. The sodium hydride had been washed with hexane to remove mineral oil. The mixture was stirred for 10 minutes. Solution B was then gradually injected into the mixture solution, also using a syringe. The mixture was stirred again for 14 hours, and the solvent was removed by evaporation. The residue was dissolved in ethyl ether and filtered to obtain filtrate, which was rinsed with water to collect the organic layer. After the solvent was removed, the product was subject to column chromatography (hexane/ethyl acetate/chloroform 3/1/1), and the middle portion was collected. The product was represented by the following formula:

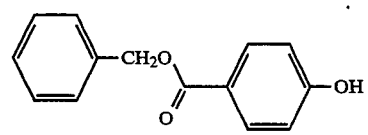

The yield was 75%.

Step B

To a solution containing 3.35 g (11 mmol) of the compound obtained from Step A and 1.6 g (10 mmol) of an optically active organic acid represented by the following formula:

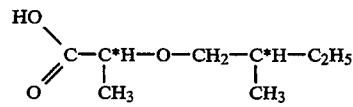

in 25 ml of dry dichloromethane, 0.12 g (1 mmol) of 4-(N,N-dimethylamino) pyridine (DMAP) and 2.3 g (11 mmol) of dicyclohexylcarbodiimide (DCC) were added. The mixture was stirred at room temperature under nitrogen for 10-14 hours. After the precipitate was removed, the filtrate was added with equal amount of dichloromethane, and washed with dilute hydrochloric acid, then deionized water. The final product, which was purified by liquid column chromatography (hexane/ethyl acetate 4/1), was presented by the following formula:

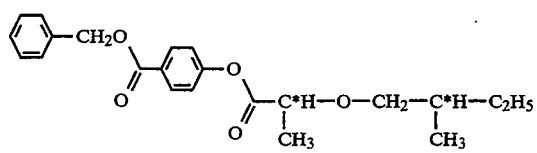

Step C

To a solution containing 5 mmol of the product from Step B in 80 ml of ethanol, 40 ml of cyclohexene and 0.4–0.5 g of 10% Pd/C were added. The solution was stirred at room temperature overnight. The Pd/C was removed via filtration with Celite. Compound 1 was then obtained after the solvent was removed by vaporization. The yield was about 95%. While this purity was generally good enough to conduct next step reactions, further purification may be achieved using ethanol or hexane crystallization.

EXAMPLE 1

In Example 1, the ferroelectric liquid crystal compound that was prepared can be represented by formula (I) as having R=decyl group, R'=ethyl group, D=hydrogen atom, x=1, y=1, and A=—CO—

The first step of the reaction in Example 1 involved preparing reaction solution A. 2.8 g (2.8 mmol) of compound 1 as prepared above was dissolved in 10 ml benzene. Then 10 mmol of oxalyl chloride ($COCl_2$) was slowly added to the solution in 10 minutes. A drop of dimethylformamide (DMF) was also added as a catalyst. The solution was stirred at room temperature for three hours and was placed in a 30 mm Hg vacuum to remove excess oxalyl chloride. The reaction mixture was returned to normal pressure by introducing dry nitrogen. Thereafter, 10 ml dichloromethane was added to the solution to form reaction solution A.

In a separate step, reaction solution B was prepared by dissolving compound 2, which is represented by the following formula:

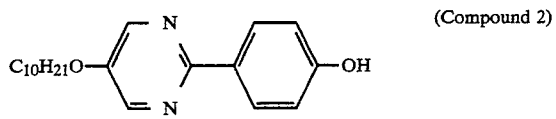
(Compound 2)

into a solution mixture containing 1 ml of pyridine and 10 ml of dichloromethane. This formed reaction solution B.

Solution B was slowly added into solution A in five minutes. The mixture solution was stirred for twelve hours, and then placed in a vacuum to remove solvent. After recrystalization using hexane, 4.0 g of solid product, which had the following formula:

171.37, 163.97, 161.69, 156.96 (2C)154.65, 152.59, 135.40, 132.98, 131.80 (2C), 129.16 (2C), 127.06, 121.66 (2C), 121.62 (2C), 75.87, 75.12, 35.06, 31.82, 30.71, 30.11, 29.51 (2C), 29.47, 29.29, 29.25, 28.99, 26.05, 22.62, 18.55, 16.44, 14.07, 11.20;

IR (KBr) $\nu$ max:
2927, 1775, 1742, 1604, 1504, 1161, 1057, 890 cm$^{-1}$
MS (m/z, relative intensity)
Theoretical: ($C_{35}H_{46}N_2O_5$, 574)
Measured: ($C_{26}H_{40}N_2O_2$, 574)
Elemental Analysis (%)
Theoretical: (C:73.14, H:8.07, N:4.87)
Measured: (C:73.17, H:8.08, N:4.88)

EXAMPLE 2

In Example 2, the ferroelectric liquid crystal compound that was prepared can be represented by formula (I) as having R=decyl group, R'=ethyl group, D=hydrogen atom, x=0 y=0 and A=—CO—

The first step of the reaction in Example 2 involved preparing reaction solution C. Compound 4, which was represented by the following formula:

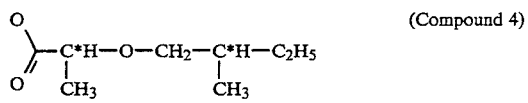
(Compound 4)

was dissolved in 10 ml benzene. Then 10 mmol of oxalyl chloride ($COCl_2$) was slowly added to the solution in 10 minutes. A drop of dimethylformamide (DMF) was also added as a catalyst. The solution was stirred at room temperature for three hours and was placed in a 30 mm Hg vacuum to remove excess oxalyl chloride. The reaction mixture was returned to normal pressure by introducing dry nitrogen. Thereafter, 10 ml of dichlorometh-

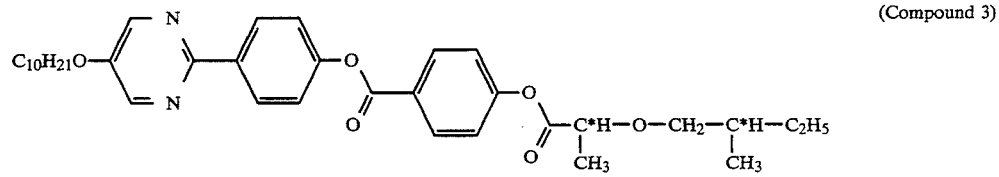
(Compound 3)

was obtained. The above reaction had a yield of 70%. The product, designated as compound 3, had an optical rotation $[\alpha]_D^{25} = -34°$ (c=1.0, $CHCl_3$). The analytical results obtained from compound 3 are summarized below:

$[\alpha]_D^{25} = -34°(c=1, CHCl_3)$ $^1$H NMR ($CDCl_3$) $\delta$:
($CDCl_3$)$\delta$8.60 (s, 2H), 8.49 (d, 2H, J 8.8), 8.24 (d, 2H, J 8.8), 7.40~7.20 (peaks overlapped, 4H), 4.17 (q, 1H, J 6.9), 3.56 (AB d, 1H, J 8.7 6.2), 3.24 (AB d, 1H, J8.7 6.6), 2.59 (t, 2H, J 7.9), 1.80~1.05 (peaks overlapped, 22H), 1.05~0.80 (peaks overlapped, 9H);

$^{13}$C NMR ($CDCl_3$) $\delta$:

ane was added to the solution to form reaction solution A.

In a separate step, reaction solution B was prepared by dissolving compound 2 as described in Example 1 into a solution mixture containing 1 ml of pyridine and 10 ml of dichloromethane. This formed reaction solution B.

Solution B was slowly added into solution A in five minutes. The mixture solution was stirred for twelve hours, and then placed in a vacuum to remove solvent. After recrystalization using hexane, 4.0 g of a solid product was obtained. The procedure in Example 2 was very similar to that in Example 1, except that Compound 4 instead of Compound 1 was used in the reaction. The final product is represented by the following formula as Compound 5:

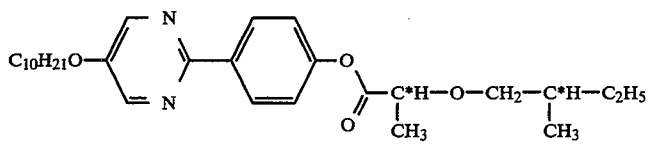

The above reaction had a yield of 68%. The reaction product had an optical rotation $[\alpha]_D^{25} = -42°$ (c=1.16, CHCl₃). The analytical results obtained from the reaction product are summarized below:

$[\alpha]_D^{25}$: −42(conc.=1.16, CHCl₃)

¹H NMR (CDCl₃) δ:
8.61 (s, 2H), 8.46 (d, 2H, J 8.8), 7.23 (d, 2H, J 8.8), 4.18 (t, 1H, 6.8), 3.59 (AB d, 1H, J 8.8 6.2), 3.26 (AB d, 1H, J8.8 6.6), 2.61 (t, 2H, J7.8), 1.8~1.05 (peaks overlapped, 22H), 1.05~0.8 (peaks overlapped, 9H);

¹³C NMR (CDCl₃) δ:
171.79, 161.69, 157.0(2C), 152.29, 135.42, 133.02, 129.14 (2C), 121.40 (2C), 75.86, 75.22, 35.10, 31.86, 30.74, 30.15, 29.49 (2C), 29.27 (2C), 29.02, 26.11, 22.65, 18.64, 16.48, 14.08, 11.24;

IR (KBr) ν max:
2926, 2856, 1777, 1587, 1546, 1430, 1198, 1160, 1121, 884 cm⁻¹

MS (m/z):455 (M+, 15.0)

EXAMPLES 3-12

Seven different optically active compounds and five different ferroelectric liquid crystals were prepared according to the procedures described in Example 1. In all these examples, the compounds can be represented by formula (I) as having R'=ethyl group, D=hydrogen atom, and A=—CO—. R, x and y are variable. The liquid crystal temperature, phase transition temperature, and optical rotation of the twelve compounds prepared from Examples 1-14 are summarized in Table 1. These liquid crystal compositions were sandwiched between two electrode glass substrates, the gap between the two glass substrates was 2 microns. Their spontaneous polarizations were measured using a method disclosed in Jap. J. Appl. Phys., 1983, 22, L661. The response times were measured using a triangular wave method disclosed in Mol. Cryst. Liq. Cryst., 1984, 114, 283. The results of spontaneous polarization and response time are also summarized in Table 1.

EXAMPLE 13

In Example 13, the compound that was prepared can be represented by formula (I) as having R=octyl group, R'=ethyl group, D=hydrogen atom, x=0, y=0 and A=—CH₂—

0.36 g of potassium hydroxide (6.4 mmol) and 15 ml ethanol were mixed and stirred while heating at 60° C. until total dissolution. To the solution mixture, 1.4 g of Compound 7a, which was represented by the following formula:

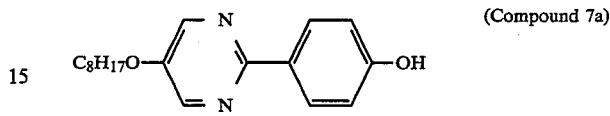

dissolved in 2 ml of ethanol was added and stirred for another 15 minutes. Then 1.55 g (5.2 mmol) of Compound 6, which was represented by the following formula:

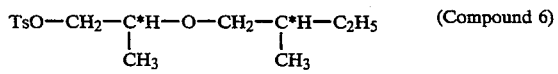

was added, drop by drop to the mixture solution. The mixture was stirred under reflux overnight. After it was cooled, the pressure was reduced to remove ethanol. The residual liquid was rinse with dichloromethane. After neutralizing with 10% HCl in aqueous solution, the organic layer was removed and its pH was adjusted using saturate sodium bicarbonate to a slightly basic condition, followed by rinsing with deionized water twice and dried with anhydrous magnesium sulfate. After filtration and concentration, an oily raw product was obtained. The raw product was purified using flash chromatography (eluent: n-hexane/ethyl acetate=10/1), and 712 mg (1.72 mmol) of an oily transparent liquid product, which is represented by the following formula, was obtained:

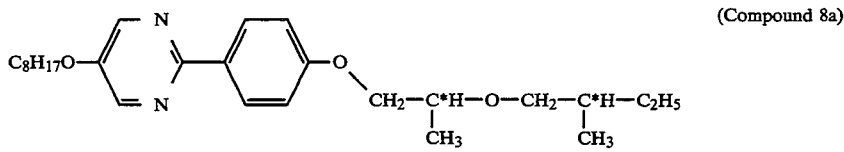

The analytical results of the product obtained above are summarized below.

$[\alpha]_D^{25}$: −15 (conc.=1, CHCl₃)

¹H NMR (CDCl₃) δ:
8.55(s,2H), 8.33(dd, J1=6.9 Hz, J2=2.1, 2H), 6.98(dd, J1=7.0 Hz, J2=2.1 Hz, 2H), 3.97(m,2H), 3.78(m, 1H), 3.36(m, 2H), 2.58(t,J=7.6 Hz,2H) 1.61(m, 2H), 1.39(m, 1H), 1.28(m, 6×2H), 0.87(overlapped peaks 4×3H)

¹³C NMR (CDCl₃) δ:
163.13(1c), 161.65(1c), 157.65(2c), 132.83(1c), 131.08(1c), 130.06(2c), 115.23(2c), 76.63(1c), 74.62(1c), 72.39(1c), 35.93(1c), 32.51(1c), 31.52(1c), 30.85(1c), 30.01(1c), 29.89(1c), 29.73(1c), 26.90(1c), 23.34(1c), 18.03(1c), 17.28(1c), 14.78(1c), 12.00(1c)

IR (neat) ν max:

2960, 2928, 2857, 1608, 1585, 1430, 1253, 1168, 1106, 798

MS (m/z)

Theoretical: ($C_{26}H_{40}N_2O_2$, 412)

Measured: ($C_{26}H_{40}N_2O_2$, 412)

Elemental Analysis (%)

Theoretical: (C:75.68, H:9.77, N:6.79)

Measured: (C:75.71, H:9.80, N:6.86)

EXAMPLE 14

In Example 14, the compound that was prepared can be represented by formula (I) as having R=octyl group, R'=ethyl group, D=hydrogen atom, x=1, y=0 and A=—$CH_2$—

0.16 g of potassium hydroxide (2.8 mmol) and 8 ml of ethanol were mixed and stirred while heating at 60° C. until total dissolution. To the solution mixture, 0.72 g of Compound 9a, which is represented by the following formula:

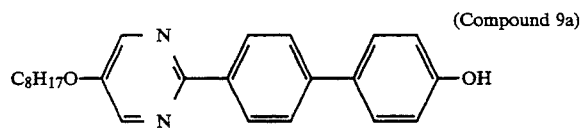

(Compound 9a)

dissolved in 2 ml ethanol was added and stirred for another 15 minutes. Then 1.55 g (5.2 mmol) of Compound 6 was added, drop by drop to the mixture solution. The mixture was stirred under reflux overnight. After it was cooled, the system pressure was reduced to remove ethanol. The residual liquid was rinsed with dichloromethane. After neutralizing with 10% HCl in aqueous solution, the organic layer was removed and its pH was adjusted using saturated sodium bicarbonate to a slightly basic condition, followed by rinsing twice with deionized water and dried with anhydrous magnesium sulfate. After filtration and concentration, a raw product was obtained. The raw product was purified using flash chromatography (eluent: n-hexane/ethyl acetate/chloroform=8/1/1), and 671 mg (1.4 mmol) of a white solid product, which is represented by the following formula as Compound 10a, was obtained:

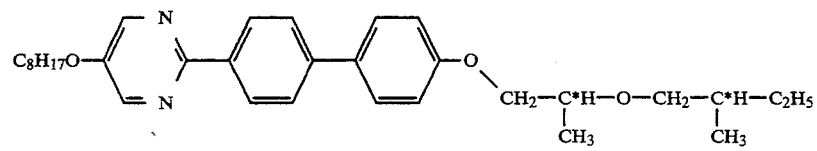

(Compound 10a)

The analytical results of the product obtain are summarized below.

$[\alpha]_D^{25}$: —17(conc.=1, $CHCl_3$)

$^1H$ NMR ($CDCl_3$) δ:
8.62(s,2H), 8.44(d, J=8.4 Hz,2H), 7.67 (d, J=8.5 Hz, 2H), 7.60(d, J=8.7 Hz, 2H), 7.00 (d, J=8.7 Hz, 2H), 3.97(m,2H), 3.78 (m, 1H), 3.38 (m,2H), 2.62(t, J=7.3 Hz, 2H), 1.62 (m,2H), 1.51-1.13(m, 1H), 1.26(m, 6×2H), 0.89(overlapped peaks, 4×3H)

$^{13}C$ NMR ($CDCl_3$) δ:
163.21(1c), 159.74(1c), 157.95(2c), 143.50(1c), 136.86(1c), 133.97(1c), 133.73(1c), 129.17(2c), 129.04(2c), 127.65(2c), 115.85(2c), 75.82(1c), 74.86(1c), 72.64(1c), 36.14(1c), 32.72(1c), 31.72(1c), 31.12(1c), 30.22(1c), 30.10(1c), 29.97(1c), 27.11(1c), 23.55(1c), 18.27(1c), 17.49(1c), 15.00(1c), 12.22(1c)

IR (KBr) ν max:
2961, 2925, 2871, 2848, 1605, 1500, 1439, 1253, 825, 795

MS (m/z)

Theoretical: ($C_{32}H_{44}N_2O_2$, 488)

Measured: ($C_{32}H_{44}N_2O_2$, 488)

Elemental Analysis (%)

Theoretical: (C:78.65, H:9.07, N:5.73)

Measured: (C:78.50, H:9.08, N:5.73)

EXAMPLE 15

In Example 15, the compound that was prepared can be represented by formula (I) as having R=octyl group, R'=ethyl group, D=hydrogen atom, x=1, y=0 and A=—$CH_2$—

0.13 g (0.5 mmol) of Compound 7b, which is represented by the following formula:

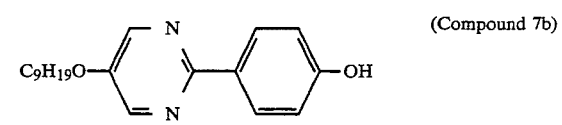

(Compound 7b)

,0.15 g (0.5 mmol) of Compound 11, which is represented by the following formula:

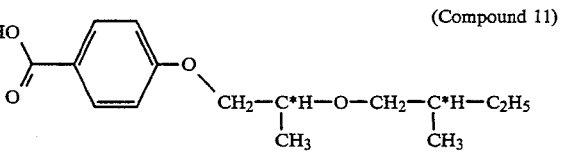

(Compound 11)

,0.16 g (0.75 mmol) of N,N'-dicyclohexylcarbodiimide, 0.01 g (0.1 mmol) of 4-(dimethylamino)pyridine and dried dichloromethane were mixed and stirred at room temperature for 20 hours. After the white solid was filtered out, the liquid filtrate was rinsed twice with deionized water. To the organic layer, anhydrous magnesium sulfate was added. After filtration and concentration, a raw product was obtained. The raw product was purified using flash chromatography (eluent: n-hexane/dichloromethane/ethyl acetate=17/2/1), and 0.23 g (1.4 mmol of a white solid product, which is represented by the following formula as Compound 12b, was obtained, representing a reaction yield of 85%:

(Compound 12b)

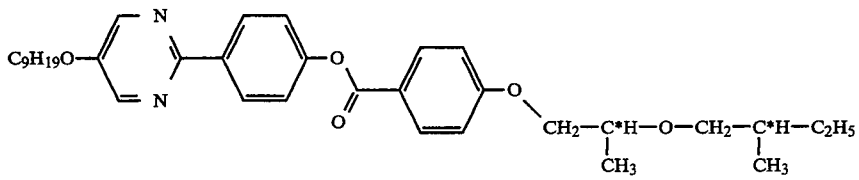

The analytical results of the product obtained are summarized below.

$[\alpha]_D^{25}$: −13 (conc.=1, CHCl$_3$)

$^1$H NMR(CDCl$_3$) δ:
8.60(s,2H), 8.47(d, J=8.8 Hz,2H), 3.99 (m,2H), 3.79(m, 1H), 3.36(m, 2H), 2.61 (t, J=7.6 Hz, 2H), 1.60(m,2H), 1.25(m,7×2H), 1.46–1.18(m, 1H), 0.87(overlapped peaks, 4×3H)

$^{13}$C NMR(CDCl$_3$) δ:
165.59(1c), 164.26(1c), 162.81(1c), 157.97(1c), 153.85(1c), 136.10(1c), 133.88(1c), 133.22(2c), 130.063(2c), 122.80(2c), 122.63(1c), 115.36(2c), 75.86(1c), 74.72(1c), 72.73(1c), 36.12(1c), 32.77(1c), 31.72(1c), 31.12(1c), 30.41(1c), 30.27(1c), 30.19(1c), 29.97(1c), 27.10(1c), 23.58(1c), 18.11(1c), 17.49(1c), 15.03(1c), 12.23(1c)

IR (KBr) ν max:
2960, 2931, 2854, 1731 (C=O), 1606, 1585, 1548, 1511, 1454, 1435, 1315, 1291, 1260, 1202, 1174, 1164, 1076, 1057, 989

MS (m/z)
Theoretical: (C$_{34}$H$_{46}$N$_2$O$_4$, 546)
Measured: (C$_{34}$H$_{46}$N$_2$O$_4$, 546)
Elemental Analysis (%)
Theoretical: (C:74.69, H:8.48, N:5.12)
Measured: (C:74.60, H:8.47, N:5.21)

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 1

| Compound | R | x | y | \multicolumn{8}{c|}{Liquid Crystal Phase and Transition Temperature (°C.)} | \multicolumn{3}{c|}{Physical Characteristics} |
|---|---|---|---|---|---|---|---|---|---|---|---|---|---|---|
| | | | | K | | Sc* | | S$_A$ | | N* | | I | Ps(nC/cm$^2$) | τ(µs) | $[\alpha]_D^{25}$ (CHCl$_3$) |
| 3a | C$_6$H$_{13}$ | 1 | 1 | * | 59 | — | | — | * | 76 | | * | — | — | −33 |
| 3b | C$_7$H$_{15}$ | 1 | 1 | * | 47 | * | 60 | — | * | 88 | | * | 41 | 78 | −34 |
| 3c | C$_8$H$_{17}$ | 1 | 1 | * | 50 | * | 63 | — | * | 86 | | * | 7 | 37 | −34 |
| 3d | C$_9$H$_{19}$ | 1 | 1 | * | 56 | * | 83 | — | * | 92 | | * | 15 | 43 | −33 |
| 3e | C$_{10}$H$_{21}$ | 1 | 1 | * | 63 | * | 84 | — | * | 90 | | * | 20 | 43 | −34 |
| 3f | C$_{11}$H$_{23}$ | 1 | 1 | * | 73 | * | 89 | — | * | 92 | | * | 40 | 40 | −34 |
| 5a | C$_6$H$_{13}$ | 0 | 0 | * | 20 | — | | — | | — | | * | — | — | −40 |
| 5b | C$_7$H$_{15}$ | 0 | 0 | * | 25 | — | | — | | — | | * | — | — | −39 |
| 5c | C$_8$H$_{17}$ | 0 | 0 | * | 28 | — | | — | | — | | * | — | — | −42 |
| 5d | C$_9$H$_{19}$ | 0 | 0 | * | 28 | — | | — | | — | | * | — | — | −43 |
| 5e | C$_{10}$H$_{21}$ | 0 | 0 | * | 32 | — | | — | | — | | * | — | — | −42 |
| 5f | C$_{11}$H$_{23}$ | 0 | 0 | * | 36 | — | | — | | — | | * | — | — | −43 |

Note:
K represents solid state; Sc* represents chiral smectic C phase; S$_A$ represents smectic A phase; N* represents chiral nematic phase; I represents liquid phase; Ps represents spontaneous polarization; τ represents response time. Both Ps and τ were measured at a temperature which was 10° C. below the phase transition temperature between Sc* and N* phases at an external voltage of ±20 volts, 50 Hz.

TABLE 2

| Compound | R | x | y | \multicolumn{8}{c|}{Liquid Crystal Phase and Transition Temperature (°C.)} | Optical Rotation |
|---|---|---|---|---|---|---|---|---|---|---|---|---|---|
| | | | | K | | Sc* | | S$_A$ | | N* | | I | $[\alpha]_D^{25}$ (CHCl$_3$) |
| 8a | C$_8$H$_{17}$ | 0 | 0 | * | 23 | — | | — | | — | | * | −15 |
| 8b | C$_9$H$_{19}$ | 0 | 0 | * | 20 | — | | — | | * | 23 | * | −15 |
| 8c | C$_{10}$H$_{21}$ | 0 | 0 | * | 28 | — | | — | | — | | * | −15 |
| 10a | C$_8$H$_{17}$ | 1 | 0 | * | 78 | — | | * | 112 | — | | * | −17 |
| 10b | C$_9$H$_{19}$ | 1 | 0 | * | 74 | — | | * | 123 | — | | * | −19 |
| 10c | C$_{10}$H$_{21}$ | 1 | 0 | * (S$_B$) | 75 (89) | * | 115 | * | 119 | — | | * | −16 |
| | | | | * (S$_F$) | (84) | | | | | | | | |
| 12a | C$_8$H$_{17}$ | 1 | 1 | * | 73 | — | | — | | * | 81 | * | −12 |
| 12b | C$_9$H$_{19}$ | 1 | 1 | * | 72 | — | | — | | * | 89 | * | −13 |
| 12c | C$_{10}$H$_{21}$ | 1 | 1 | * | 61 | — | | — | | * | 91 | * | −12 |

Note:
K represents solid state; Sc* represents chiral smectic C phase; S$_A$ represents smectic A phase; S$_B$* represents chiral smectic B phase; S$_F$* represents chrial smectic F phase; N* represents chiral nematic phase; I represents liquid phase.

What is claimed is:
1. An optically active liquid crystal compound represented by the following formula:

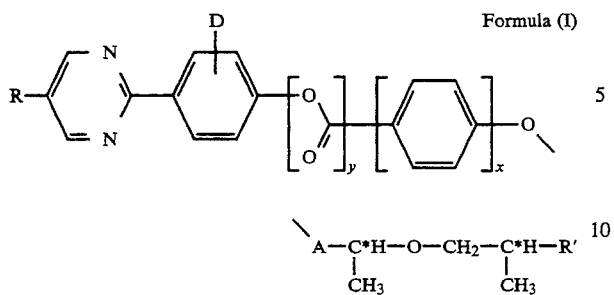

Formula (I)

wherein:

A: is selected from the group consisting of —CH₂— and —CO—;

R: is an alkyl or alkoxyl group having 1 to 22 carbons;
R': is an alkyl group having 2 to 8 carbons;
x,y: are integers of either 0 or 1, provided that when x=0, y≠1;
D: is selected form the group consisting of hydrogen and halogen atoms; and
*: represents a chiral center.

2. The optically active liquid crystal compound of claim 1 wherein R is a linear alkyl group having 3 to 12 carbons.

3. The optically active liquid crystal compound of claim 1 wherein R is a linear alkoxyl group having 3 to 12 carbons.

4. The optically active liquid crystal compound of claim 1 wherein D is an hydrogen or fluorine atom.

5. The optically active liquid crystal compound of claim 1 wherein R' is an ethyl group.

6. The optically active liquid crystal compound according to claim 1 which is represented by the following formula:

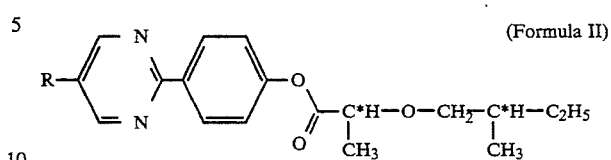

(Formula II)

wherein R is an alkyl group having 1 to 22 carbons and * represents a chiral center.

7. The optically active liquid crystal compound according to claim 1 which is an ferroelectric liquid crystal and represented by the following formula:

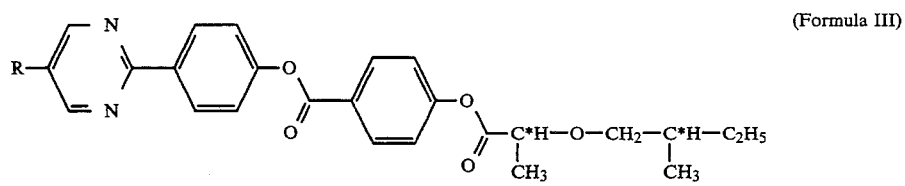

(Formula III)

wherein R is an alkyl group having 1 to 22 carbons and * represents a chiral center.

8. The optically active liquid crystal compound according to claim 1 which is represented by the following formula:

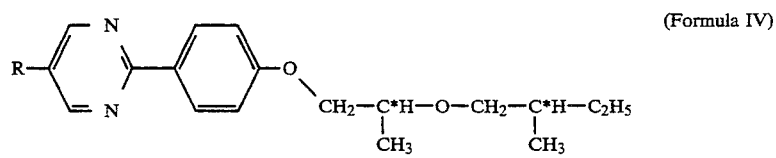

(Formula IV)

wherein R is an alkyl group having 1 to 22 carbons and * represents a chiral center.

9. The optically active liquid crystal compound of claim 1 which is represented by the following formula:

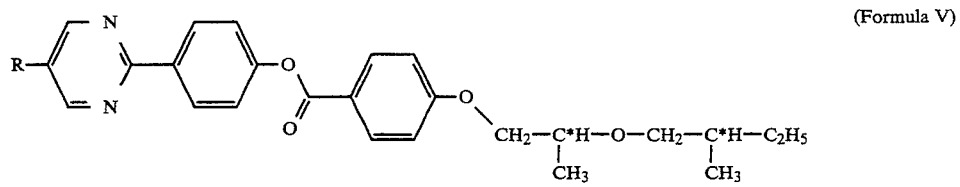

(Formula V)

wherein R is a linear alkyl group having 1 to 22 carbons and * represents a chiral center.

10. The optically active liquid crystal compound of claim 1 which is represented by the following formula:

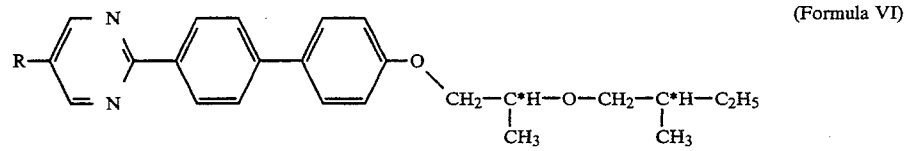

(Formula VI)

wherein R is a linear alkyl group having 1 to 22 carbons and * represents a chiral center.

11. A liquid crystal composition comprising an optically active liquid crystal compound represented by the following formula:

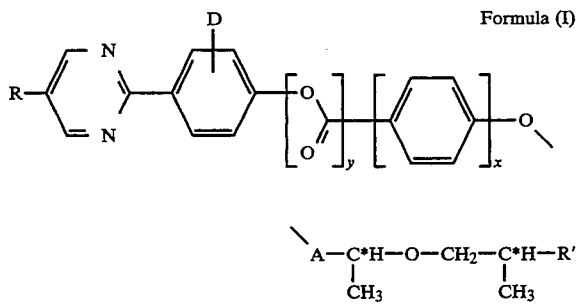

Formula (I)

wherein:

A: is selected from the group consisting of —CH$_2$— and —CO—;
R: is an alkyl or alkoxyl group having 1 to 22 carbons;
R': is an alkyl group having 2 to 8 carbons;
x,y: are integers of either 0 or 1, provided that when x=0, y≠1;
D: is selected form the group consisting of hydrogen and halogen atoms; and
*: represents a chiral center.

12. The liquid crystal composition of claim 11 which further comprises a smectic C phase liquid crystal or a chiral smectic C phase liquid crystal, or a mixture thereof.

13. The liquid crystal composition of claim 11 which is placed between a pair of substrates and is adapted tier use in a liquid crystal device.

14. The liquid crystal composition of claim 11 which is used in a liquid crystal light switching device.

* * * * *